United States Patent [19]
Rosenthal et al.

[11] Patent Number: 6,042,600
[45] Date of Patent: Mar. 28, 2000

[54] RADIOACTIVE MEDICAL DEVICES FOR INHIBITING A HYPERPLASTIC RESPONSE OF BIOLOGICAL TISSUE

[76] Inventors: David Rosenthal, 341 Lands Mill SE., Marietta, Ga. 30067; Stephen A. Sosnowski, 2958 Ora Avo Terr., Vista, Calif. 92084

[21] Appl. No.: 09/236,756

[22] Filed: Jan. 25, 1999

Related U.S. Application Data

[63] Continuation-in-part of application No. 08/837,710, Apr. 22, 1997, Pat. No. 5,897,573
[60] Provisional application No. 60/016,360, Apr. 26, 1996.

[51] Int. Cl.⁷ .................................................... A61B 17/04
[52] U.S. Cl. ................................ 606/224; 606/228; 600/3
[58] Field of Search ..................................... 606/222–224, 606/228; 600/1, 3

[56] References Cited

U.S. PATENT DOCUMENTS 3,943,933   3/1976   Gertzman ................................ 606/224

OTHER PUBLICATIONS

Intracoronary Irradiation Markedly Reduces Restenosis After Balloon Angioplasty in a Porcine Model, Journal of the American College of Cardiology, vol. 23, No. 6, pp. 1491–1498, May 1994; Joseph G. Wiedermann, MD, Charles Marboe, MD, Howard Amols, PhD, Allan Schwartz, MD, FACC, Judah Weinberger, MD, PhD, FACC.

High Dose Rate Brachytherapy for Prevention of Restenosis After Percutaneous Transluminal Coronary Angioplasty: Preliminary Dosimetric Tests of a New Source Presentation, Int. J. Radiation Biol. Phys., vol. 33, No. 1, pp. 211–215, 1995; Youri Popowski, M.D., Vitali Verin, M.D., Igor Papirov, Philippe Nouet, Michel Rouzaud, Eugene Grob, Michael Schwager, Philippe Urban, M.D., Wilhelm Rutishauser, M.D. and John M. Kurtz, M.D.

Endovascular Irradiation—A New Method to Avoid Recurrent Stenosis After Stent Implantation in Peripheral Arteries: Technique and Preliminary Results, Int. J. Radiation Oncology Biol. Phys., vol. 29, No. 1, pp. 183–186, 1994; H.D. Bottcher, M.D., B. Schopohl, M.D., D. Liermann, M.D., J. Kollath, M.D. and I.A. Adamietz, M.D.

Prophylactic Endovascular Radiotherapy to Prevent Intimal Hyperplasia after Stent Implantation in Femoropopliteal Arteries, Cardio Vascular and Interventional Radiology, vol. 17, pp. 12–16, 1994; Dieter Liermann, Heinz D. Bottcher, Jürgen Kollath, Bernd Schopohl, Gerd Strassman, Ernst P. Strecker, Karl H. Breddin.

*Primary Examiner*—Gary Jackson
*Attorney, Agent, or Firm*—Thomas, Kayden, Horstemeyer & Risley

[57] ABSTRACT

Generally described, the present invention comprises a medical device for implantation in biological tissue and a method of making the medical device. The medical device comprises an organic compound forming at least a portion of the medical device and a beta radiation emitting element chemically bonded to the organic compound of the medical device. The beta emitter preferably causes the medical device to generate a beta radiation greater than 0.0002 μCi/cm. The beta radiation emitting element can be tritium preferably incorporated into the organic compound of the medical device by a Wilzbach process. The Wilzbach process involves an entropic exchange of the beta emitting element for elemental hydrogen in a vacuum sealed reaction chamber. On the other hand, the beta radiation emitting element may comprise Carbon 12, or other similar beta emitter, which is incorporated directly into the backbone of the organic compound prior to manufacturing the medical device from the organic compound. In another aspect of the present invention, rather than placing the medical device itself in a reaction chamber for incorporation of a beta emitting element, a mass of organic material may be placed in a reaction chamber. Again, a beta emitting element is preferably incorporated into the organic material via the Wilzbach process.

22 Claims, 3 Drawing Sheets

RADIOACTIVE MEDICAL DEVICES FOR INHIBITING A HYPERPLASTIC RESPONSE OF BIOLOGICAL TISSUE

RELATED APPLICATIONS

This application is a continuation-in-part of prior-filed application Ser. No. 08/837,710; filed Apr. 22, 1997, now U.S. Pat. No. 5,897,573, which claims priority to prior-filed provisional application Serial No. 60/016,360; filed Apr. 26, 1996. Both of the foregoing applications are incorporated herein by reference.

FIELD OF THE INVENTION

The present invention relates generally to medical devices for use in conjunction with biological tissue and, more particularly, to an apparatus and method for making and using a radioactive medical device having beta radiation emitting capabilities for inhibiting an undesired hyperplastic response to the healing of biological tissue.

BACKGROUND OF THE INVENTION

There are several devices currently used in the medical field for assisting the grafting of biological tissue. For example, sutures and "patches" are used to hold tissues in place and give the tissues time to graft, or heal. Similarly, stents come in a variety of configurations for supporting blood vessel walls in an attempt to inhibit stenosis of the vessel.

As mentioned generally, sutures are used to bring together ends of biological tissue and hold them in place until the joining tissues have time to heal. In patients with arterial occlusive disease, vascular surgeons use sutures to anastomose autogenous vein, prostehtic grafts, or arteries to other arteries in order to bypass around or replace diseased arterial segments. At virtually all anastomotic sites between the arteries and autogenous vein, or prosthetic grafts, a condition of rapid cellular growth termed "intimal hyperplasia" may occur.

Intimal hyperplasia (hereinafter "IH") is the usual response to blood vessel injury. This rapid cellular growth, as a response to injury of the blood vessel cellular lining (intima), begins to narrow (stenose) the opening (lumen) between the vessels and/or graft to the point where an occlusion may occur. More specifically, IH forms as a result of smooth muscle cell proliferation, migration, and extracellular matrix deposition. The interaction of platelets, macrophages, growth factors, and cytokines plays an important role in the process. There are systemic regimens to prevent the intimal hyperplastic response in animal models but none has proven beneficial in humans. IH is the primary cause of "restenosis" (narrowing) in the first year after vascular bypass operations and may cause indwelling venous catheters to occlude as well. Usually, the patient must have another operation to revise or replace the occluded graft. If a major vein occludes (e.g. jugular or subclavian) massive edema of the upper extremity, face and neck may occur and if an artery occludes, it could possibly lead to potential limb loss.

Of course, IH is merely a subset of a larger problem involving hyperplasia resulting from smooth muscle cell proliferation, migration, and extracellular matrix deposition. In general, when biological tissue begins grafting, or healing, an undesirable hyperplastic response may occur.

For example, in some types of medical operations, medical personnel may use "patches" to hold damaged tissue in order to give the tissue appropriate time to heal. These "patches" function in a manner similar to sutures, but are much quicker to apply and may be effective where a suture would not be appropriate. Just as with vascular bypass operations and the restenosis that may occur, the tissue held by the "patch" may also exhibit signs of hyperplasia that are undesirable, if not harmful.

The most frequently performed prosthetic graft operation is an arterial to venous conduit for dialysis in chronic renal failure patients. Renal dialysis patients require repetitive angioaccess to this arterial-venous graft for dialysis to rid their system of toxins. The most commonly used graft for dialysis is a synthetic graft made from teflon or ePTFE (expanded polytetrafluroethylene). Unfortunately, these grafts rapidly fail and have a primary occlusion rate of 15% to 50% during the first year, with a mean patency of only 15 months. This failure in most cases is due to the development of intimal hyperplasia at the venous anastomosis.

In recent years, studies have been conducted in animal models whose vessels have undergone angioplasty. It was found that the vessels response to injury from balloon angioplasty is similar to that observed at suture anastomotic lesions. Studies conducted at Emory University, Atlanta, Ga., U.S.A., and Vanderbilt University, Nashville, Tenn., U.S.A., suggest that restenosis results primarily from the migration and rapid proliferation of a smooth muscle type cell after balloon angioplasty. It has been demonstrated by these groups that very low levels of beta-particle irradiation introduced to the site of injury following angioplasty markedly inhibits smooth muscle cell proliferation and or migration. In a series of tissue culture experiments a 0.20 mm diameter titanium wire was impregnated with low concentrations of 32 P and these wires were placed in both rat and human smooth muscle cell cultures. The activity level of the wire ranged from 0.002 to 0.06 $\mu$Ci/cm wire. In comparison to the control with no radiation it was found that in cultures where the wire activity was >0.0006 $\mu$Ci/cm there was a distinct zone of complete smooth muscle cell inhibition ranging from 5.5 to 10.6 mm from the radioactive wire. It was hypothesized that if a low level radioactive wire could induce such an effect in tissue culture then a stent placed in-vivo could alter or inhibit the restenotic activity in vessels subjected to angioplasty.

Vanderbilt University in conjunction with the Walter Reed Army Medical Center performed a series of experiments in porcine iliac and coronary models utilizing radioactive Strecker stents. First results in iliac model restenosis resulted in a 37% reduction in neointimal area in 32 P 0.14 $\mu$Ci stents versus controls one month post procedure. Further in-vivo testing performed with radioactive Palmaz-Schatz stents in porcine coronary models demonstrated as much as a 50% reduction in neointimal area and cross sectional area of stenosis one month after stent implantation.

Since these early reports, numerous other studies have been conducted which have demonstrated and substantiated these early findings.

Thus, there exists a need in the art for an apparatus and method to remedy the problems and inadequacies in the prior art.

SUMMARY OF THE INVENTION

Generally described, the present invention provides a method for making and using radioactive medical devices. It is known that smooth muscle cell proliferation may be inhibited by varying degrees and types of radiation, particularly low level beta radiation. This knowledge is exploited by the novel radioactive medical devices and method described herein. Many different types of medical devices may benefit from having the capacity to emit low level localized beta radiation. Generally, any place that a plastic polymer medical device may be used in a body, the advantages afforded by the capability of emitting beta radiation may be helpful. For example, and without limitation, the medical devices of the present invention may comprise: surgical sutures, stents, surgical patches, anti-thrombogenic coatings, hydrophilic coatings, a covering or weaving over stents, fabric or mesh implants in the body, coatings on or woven into plastic catheters (e.g. dialysis catheters), and ocular lens implants.

The preferred embodiment of the present invention comprises a medical device for implantation in biological tissue. The medical device comprises an organic compound forming at least a portion of the medical device and a beta radiation emitting element chemically bonded to the organic compound of the medical device. The beta emitter preferably causes the medical device to generate a beta radiation greater than 0.0002 µCi/cm.

The organic compound making up the medical device can be a hydrocarbon, such as polypropylene. This is the preferred material when the medical device is a surgical suture. In such a situation, the beta radiation emitting element can be tritium ($H_3$). However, whether the beta emitter is tritium or some other radioactive isotope, the beta emitting element is preferably incorporated into the organic compound of the medical device by a Wilzbach process. The Wilzbach process involves an entropic exchange of the beta emitting element for elemental hydrogen, while the medical device is enclosed in a vacuum sealed reaction chamber.

As an alternative, the beta radiation emitting element may comprise Carbon 12 (C12), or other similar or suitable beta emitter. When using C12 as the beta emitter, the C12 is incorporated directly into the backbone of the organic compound prior to manufacturing the medical device from the organic compound. In accordance with this aspect of the present invention, the organic compound need not necessarily be a hydrocarbon, and the Wilzbach process will usually not be used to radiate the organic material.

In accordance with another aspect of the present invention, the invention involves a method of creating a medical device that inhibits a hyperplastic response in biological tissue. Generally, the method comprises providing a reaction chamber and placing the medical device in the reaction chamber. Once the device is in the reaction chamber, a beta radiation emitting element is introduced into the chamber. Introduction of this element causes an entropic exchange process of the beta radiation emitting element for elemental hydrogen in the medical device.

As can be seen, the method may comprise the well-known Wilzbach procedure of placing the medical device in a reaction chamber and then creating a vacuum in the reaction chamber by means of a vacuum pump. An ionized beta radiation emitting element is introduced into the chamber for causing an entropic exchange process wherein the beta radiation emitting element is exchanged for hydrogen in the material of the medical device. After introduction of the beta emitting element, the chamber is preferably sealed for a predetermined period of time. Upon completion of the reaction, the remaining beta radioisotope is removed from the chamber and the medical device is rinsed and also removed from the reaction chamber for immediate use or packaging.

In accordance with another aspect of the present invention, rather than placing the medical device itself into a reaction chamber for incorporation of a beta emitting element, a mass of organic material may be placed in a reaction chamber. A beta radiation emitting element is introduced into the chamber so that the element becomes incorporated into the organic material through an entropic exchange process. Then, the organic material can be used to manufacture the medical device needed. For example, the organic material may be extruded into a suture "thread."

Other objects, features, and advantages of the present invention will be apparent to those skilled in the art. A more thorough understanding of the invention will be gained through a review of the drawings and the detailed description set forth below.

BRIEF DESCRIPTION OF THE DRAWINGS

The present invention can be better understood with reference to the following drawings. The drawings are not necessarily to scale, emphasis instead being placed upon clearly illustrating the principles of the present invention. Moreover, like reference numerals designate corresponding parts throughout the several views.

DETAILED DESCRIPTION OF THE INVENTION

The present invention relates to conventional implantable medical devices that are designed to emit localized low-level beta radiation while in or near biological tissue. The present invention relates to both a method of preventing hyperplasia in biological tissue grafts and a method of creating medical devices that accomplish this goal. The present application is a continuation in part of prior filed application Ser. No. 08/837,710; filed Apr. 22, 1997. Application Ser. No. 08/837,710 deals with radioactive sutures and is hereby incorporated by reference as if fully set forth herein.

Although not limited to this process, the preferred method for radiating a medical device is the well-understood method of Wilzbach. Generally described, the Wilzbach method is a simple process for the random labeling of organic molecules with tritium ($H_3$) through a simple entropic exchange process. Although other radioactive isotopes may be used, tritium is the preferred radioisotope. Similarly, the present invention is not limited to incorporating a radioactive element into a medical device by only the Wilzbach method described herein. There are other methods of radiating devices that are well understood by those with skill in the art and the present invention is intended to include these other methods as well. For example, there are synthetic methods of incorporating tritium or another radioactive isotope into a given material.

Figure 1:
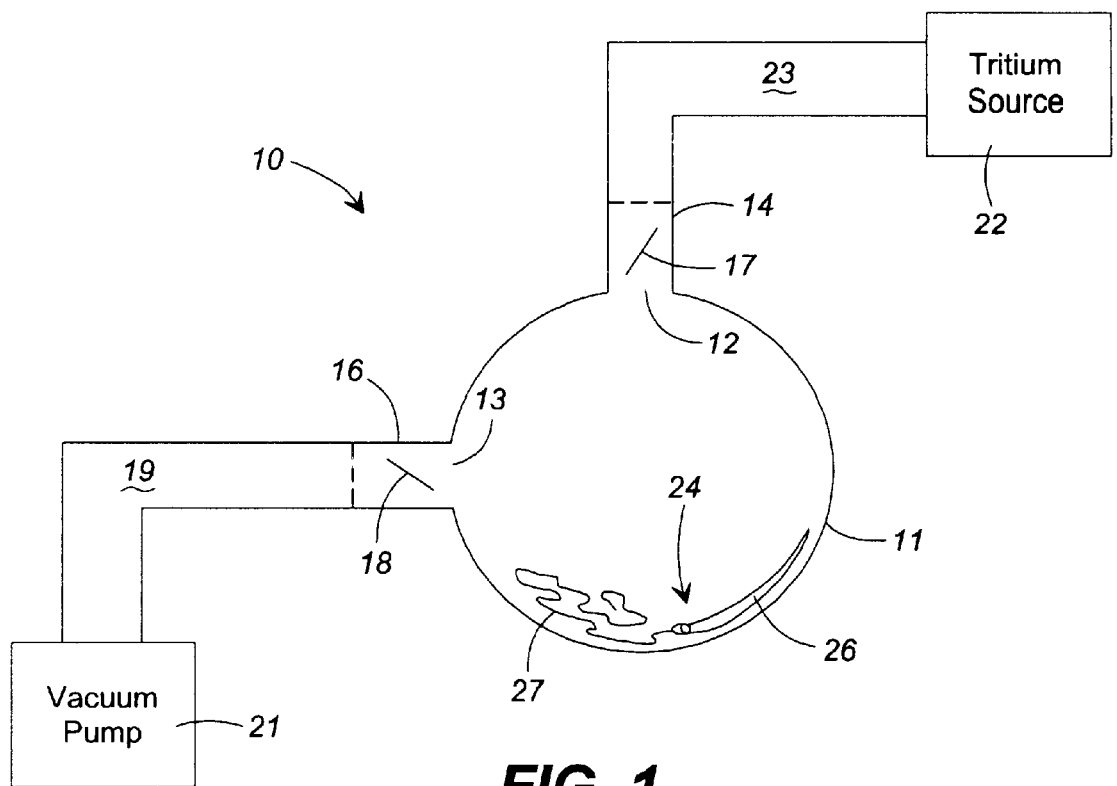
FIG. 1 is a schematic cross-sectional side view of an apparatus for radiating a medical device via the Wilzbach method.

The apparatus 10 of FIG. 1 generally depicts the preferred embodiment for incorporating a radioactive isotope into the structure of a medical device via the Wilzbach method. A reaction chamber 11 is the central element of the apparatus 10. The reaction chamber 11 of the preferred embodiment is preferably constructed of glass. Although this is not necessary to practice the present invention, glass is the preferred material due to its capacity to be flame sealed and its general non-reactivity to an entropic exchange process. This reaction chamber 11 may take a wide variety of forms and the shape of the chamber 11 is not necessarily critical to the present invention. Similarly, the size and shape of the chamber 11 may need to be altered depending on the size and mass of the item to be radiated. The reaction chamber 11 of the preferred embodiment comprises a generally spherical form having a diameter of approximately 2.5 inches.

The reaction chamber 11 is preferably fashioned to have at least one opening. As depicted in FIG. 1, the reaction chamber 11 of the preferred embodiment is constructed with an input opening 12 and an output opening 13. The input opening 12 is defined by an input cylindrical collar 14. The output opening 13 is defined by an output cylindrical collar 16. As the chamber 11 will need to be sealed during the incorporation of the radioisotope into the matrix of the medical device, both openings 12, 13 are equipped with a mechanism for sealing the openings 12, 13. In the apparatus 10 of FIG. 1, the openings 12, 13 are fitted with diaphragms 17, 18. Of course, another type of flap or covering would be appropriate with the present reaction chamber 11 and is intended to be within the scope of the present invention.

A vacuum line 19 is affixed to the output collar 16. The vacuum line 19 may be constructed of any appropriate material, such as stainless steel. The size of the line 19 is also unimportant to the first preferred embodiment of the present invention and can easily be determined by one with skill in the art. The vacuum line 19 is affixed to a vacuum pump 21. The particular vacuum pump 21 used with the first preferred embodiment is not critical to the present invention. The selection of an appropriate vacuum pump 21 may depend on the size of the reaction chamber 11 and other factors understood by those with skill in the art.

The preferred apparatus 10 also comprises a source 22 of the radioactive isotope to be used. As mentioned above, the preferred radioactive isotope is tritium. As such, a tritium source 22 is needed, along with a passageway 23 to transfer the tritium to the chamber 11.

In operation, a medical device is initially selected for incorporation of the radioactive isotope. When using the Wilzbach method of entropic exchange, the medical device to be radiated should be comprised, at least partially, of a hydrocarbon material. As the entropic exchange process substitutes the tritium "heavy hydrogen" for the hydrogen molecules of the medical device, the medical device preferably has some hydrogen molecules in its structure for the substitution. Of course, if a method other than the Wilzbach method is used to radiate the medical device, then a hydrogen composition may not be needed. The medical device may be constructed entirely of a hydrocarbon compound or merely coated with a hydrocarbon compound. As a result, any medical device, of any construction, may be radiated by the preferred method if the device is simply coated with a hydrocarbon-based compound—such as polyethylene.

Many different medical devices may benefit from having the capacity to emit localized low level beta radiation. For simplicity, a suture device has been selected as the preferred embodiment and will accordingly be depicted in the figures and described in the text concerning the first preferred embodiment. This is not intended to limit the scope of the present invention in any way. Devices such as surgical sutures, stents, surgical patches, anti-thrombogenic coatings, hydrophilic coatings, a covering or weaving over stents, fabric or mesh implants in the body, coatings on or woven into plastic catheters (e.g. dialysis catheters), and ocular lens implants may benefit from having the capacity to emit localized low level beta radiation.

Figure 2A:
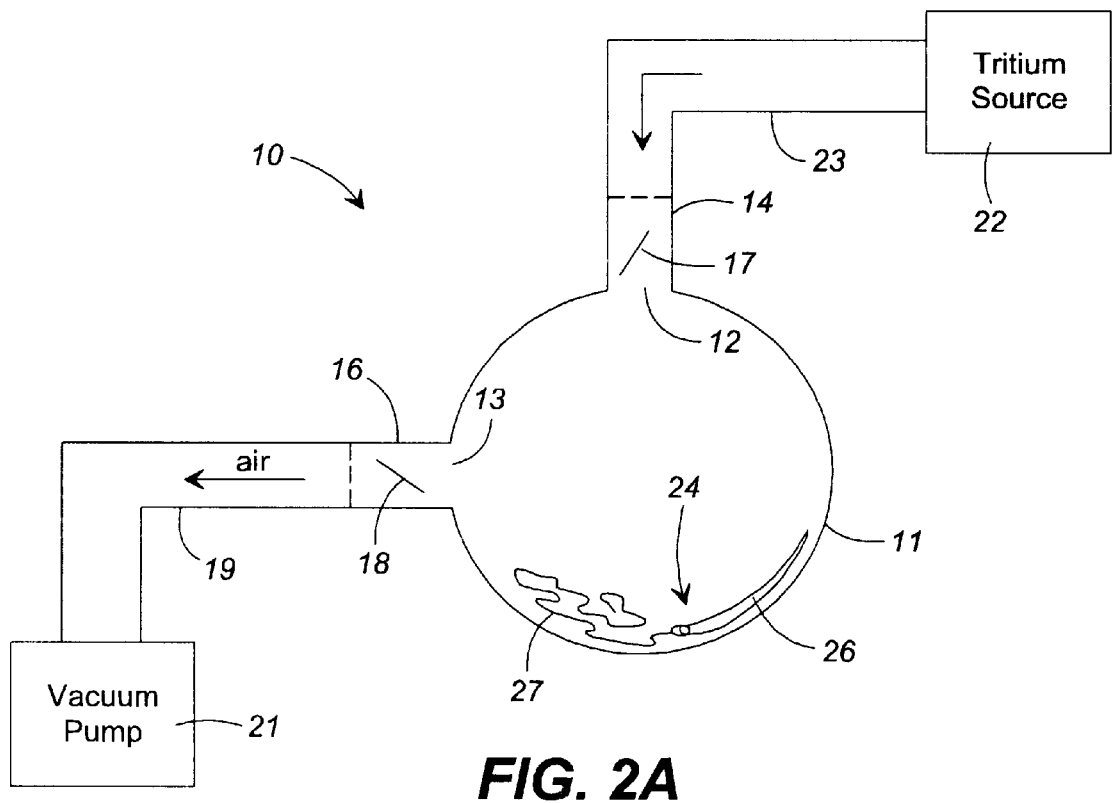
FIG. 2A is a schematic cross-sectional side view of the apparatus of FIG. 1 depicting a first step in radiating a medical device via the Wilzbach method.

As depicted in FIG. 2A, the medical device to be radiated, a suture device 24, is placed in the reaction chamber 11. The suture device 24 of the preferred embodiment comprises a stainless steel suture needle 26 and a polypropylene suture material 27. Although the suture material 27 alone may be placed in the chamber, it is preferred to attach the suture material 27 to the suture needle 26 and then place the entire suture device 24 into the reaction chamber 11. This is acceptable to the present invention as the tritium will not harm the stainless steel suture needle 26, but will impart beta radiation emitting capabilities to the suture material 27.

Once the suture device 24 is in the reaction chamber 11, the reaction chamber is evacuated by the vacuum pump 21. The vacuum pump 21 withdraws the atmosphere from the chamber 11 via the vacuum line 19, creating an atmosphereless vacuum in the chamber 11. After evacuation of atmosphere from the chamber 11, tritium is introduced from the tritium source 22 into the reaction chamber 11 via the passageway 23. The amount of tritium introduced into the chamber 11 is a matter of manufacturing preference or convenience and may vary with a variety of factors. However, the preferred level of tritium is approximately 1 Ci.

Figure 2B:
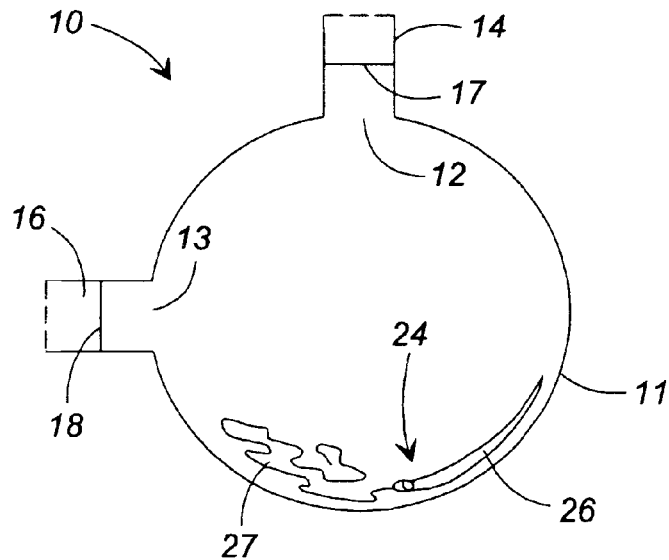
FIG. 2B is a schematic cross-sectional side view of the apparatus of FIG. 1 depicting a second step in radiating a medical device via the Wilzbach method.

After introduction of the tritium, the vacuum line 19 and the tritium source line, or passageway 23 may be disconnected and the reaction chamber 11 sealed, as shown in FIG. 2B. The diaphragms 17, 18 are positioned to close the openings 12, 13. It is preferable to flame seal these diaphragms 17, 18 as is commonly done in the art. The method of flame sealing will be understood by one with skill in the relevant art. Inside the reaction chamber 11, an entropic exchange process of tritium for hydrogen begins. In this process, the tritium is substituted into the organic matrix of the suture material 27.

The suture device 24 is allowed to remain in the sealed reaction chamber 11 for a period of anywhere from one day to several weeks, depending on the amount of tritium desired to be incorporated, which is a function of the activity level of the medical device 24 required in a particular use. One skilled in the art will be aware of the amount of tritium needed to inhibit a hyperplastic response in a particular application and can tailor the amount of time in the chamber 11 to render the desired activity level. As an example of an appropriate activity level, and not as an attempt to limit the present invention, for vascular surgical uses a suture material will typically be designed to generate beta radiation of approximately 0.00026 $\mu$Ci/cm. It has been found that beta radiation greater than 0.0002 $\mu$Ci/cm will inhibit intimal hyperplasia.

Figure 2C:
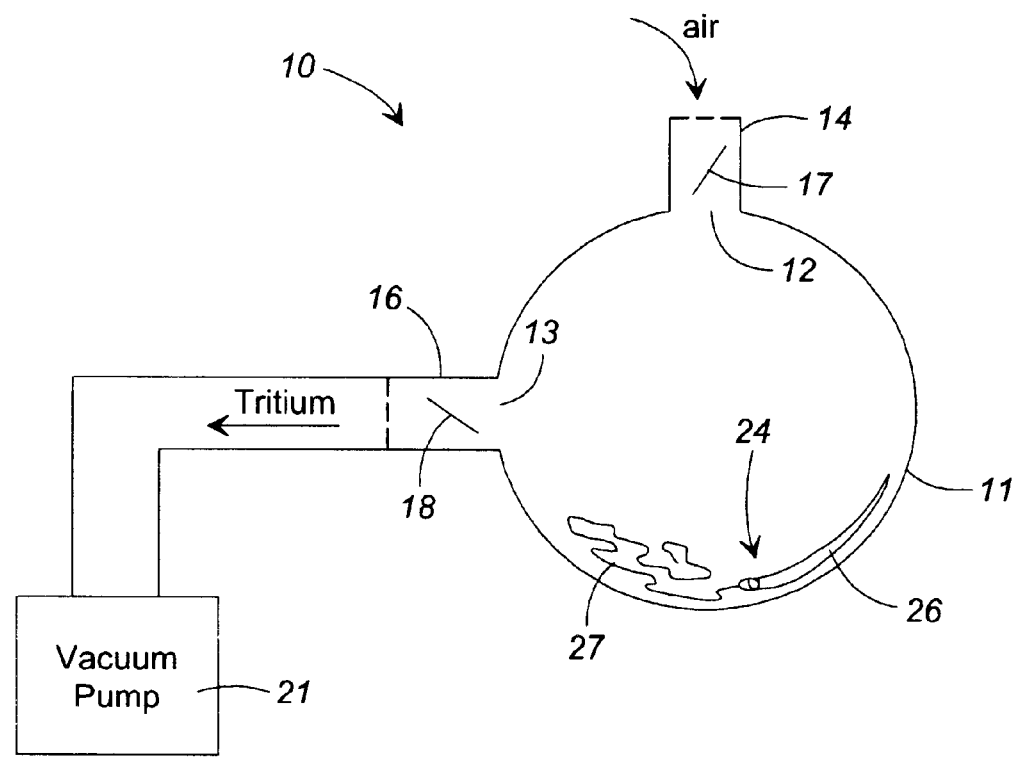
FIG. 2C is a schematic cross-sectional side view of the apparatus of FIG. 1 depicting a third step in radiating a medical device via the Wilzbach method.

Upon completion of the reaction, the reaction chamber 11 is flushed in a usual way as understood by those skilled in the art. As shown in FIG. 2C, flushing of the chamber 11 begins with evacuating the tritium remaining in the chamber 11. Then, atmosphere is introduced back into the chamber 11, removing the vacuum. The suture device 24 may then be rinsed, dried and removed from the reaction chamber 11 for immediate use or packaging for later use.

Despite the beta radiation emitting characteristics of the suture device 24, the suture material 27 does not lose its tensile strength characteristics or other physical properties. Additionally, because of the low amount of beta radiation emitted by the suture device 24, handling the device requires only the use of latex gloves. Packaging the device in a common aluminum foil pouch is sufficient to contain the radioactivity of the incorporated tritium. In this way, not only is the present invention easy to manufacture, but it is also relatively safe to handle. The medical professional may then use the radiated medical device in a variety of applications in order to take advantage of the low-level beta radiation-emitting capabilities of the medical device. Of course, the particular application will depend, to a great extent, on the particular medical device radiated.

In use, the beta-particle emitting suture of above, will be used to graft biological tissue together. As is well known in the art, sutures are commonly used to hold two portions of biological material in close proximity while the grafting of the tissue occurs. When implanted in biological tissue, the suture, having tritium in its structure, will emit low level beta radiation in a localized area around the suture. As radiation is introduced to cells surrounding the suture, the mitotic replication of these cells will be inhibited, thereby inhibiting the migration and rapid proliferation of a smooth muscle type cell. Additionally, since the vehicle for delivering the radiation is the suture itself, there is no need for injecting or implanting other radioactive substances into a site. On the other hand, the benefits of the beta emitting radiation polymer should not affect normal endothelial cell function, but will inhibit the hyperplastic response and therefore, improve graft patency and prevent early graft failure.

Although a suture device was described in reference to the first preferred embodiment of the present invention, the medical device to be radiated may comprise a wide variety of items currently used by medical professionals. Devices such as surgical sutures, stents, surgical patches, anti-thrombogenic coatings, hydrophilic coatings, a covering or weaving over stents, fabric or mesh implants in the body, coatings on or woven into plastic catheters (e.g. dialysis catheters), and ocular lens implants may be incorporated with tritium as outlined above. The same type of reaction chamber and method may be used; however, the medical device to be coated is placed within the chamber where the suture device is described above. Of course, different devices have very different size characteristics and different uses. As a result, differing levels of tritium incorporation may be desired. This can be determined by the medical professional to use the device and either the amount of tritium introduced into the chamber or the time the device is left in the chamber can be appropriately tailored.

Figure 3A:
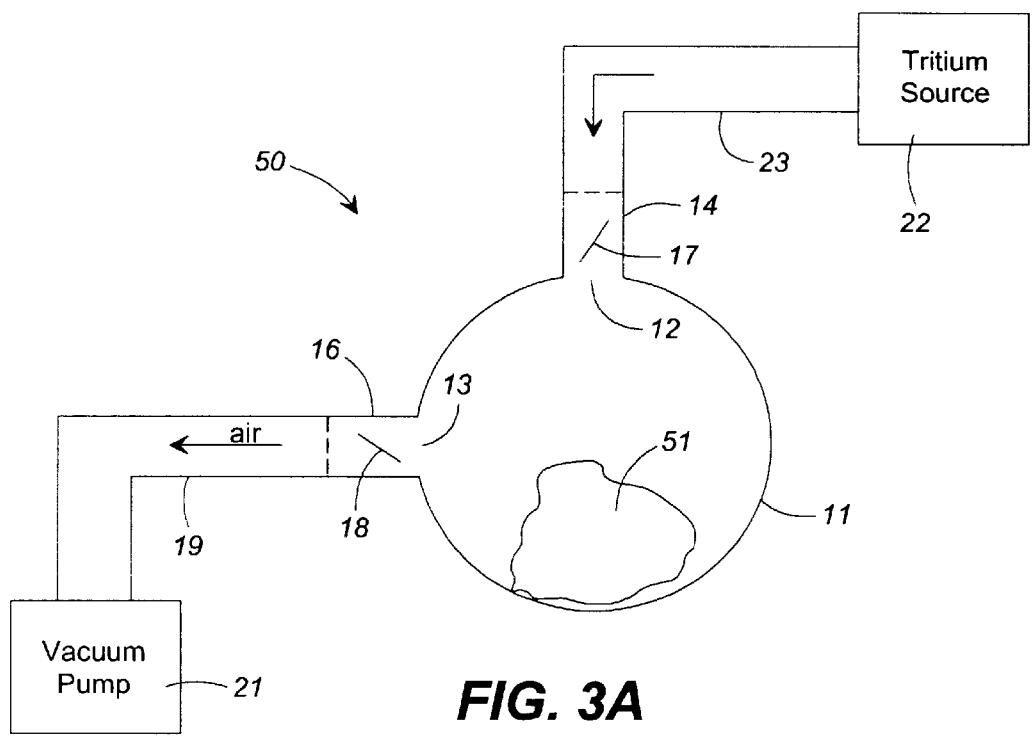
FIG. 3A is a schematic cross-sectional side view of the apparatus of FIG. 1 depicting a first step in radiating an organic mass via the Wilzbach method.

A second preferred embodiment of the present invention is depicted in FIG. 3A. The apparatus 50 of the second preferred embodiment also comprises a reaction chamber 11, a vacuum pump 21, and a tritium source 22. However, in contradistinction to the first preferred embodiment, a medical device is not placed in the reaction chamber for incorporation of tritium. Rather, a mass 51 of hydrocarbon-based material is placed in the reaction chamber. Typically, this mass 51 comprises polypropylene.

Upon placing the mass 51 in the reaction chamber 11, the reaction chamber is evacuated by the vacuum pump 21. After evacuation of the chamber 11, ionizing tritium is introduced into the reaction chamber 11, as depicted in FIG. 3A. As with the first preferred embodiment, the amount of tritium introduced into the chamber 11 is a matter of preference and may vary depending on the size of the chamber 11, the mass of the polypropylene 51, or the time of desired exposure.

Figure 3B:
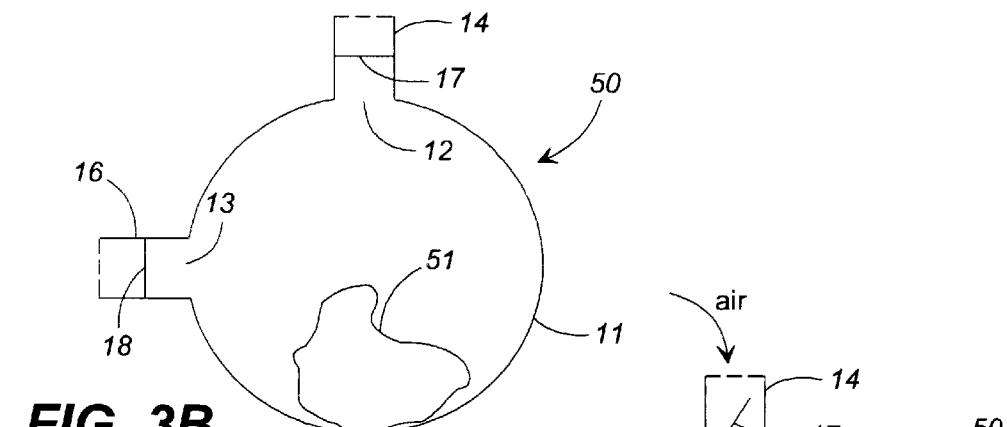
FIG. 3B is a schematic cross-sectional side view of the apparatus of FIG. 1 depicting a second step in radiating an organic mass via the Wilzbach method.

After introduction of the tritium, the reaction chamber 11 is sealed, as illustrated in FIG. 3B. The diaphragms 17, 18 are positioned to close the openings 12, 13. It is preferable to flame seal these diaphragms 17, 18 as is commonly done in the art and will be understood by one with skill in the relevant art. Inside the reaction chamber 11, an entropic exchange process of tritium for hydrogen begins. In this process, the tritium is substituted into the organic matrix of the polypropylene 51.

The polypropylene 51 is allowed to remain in the sealed reaction chamber 11 for a period of anywhere from a day to several weeks, depending on the amount of tritium desired to be incorporated and the activity level of the polypropylene 51 required in a particular use. One skilled in the art will be aware of the amount of tritium needed to repress smooth muscle cell proliferation in a particular application and can tailor the amount of time in the chamber 11 to render the desired activity level.

Figure 3C:
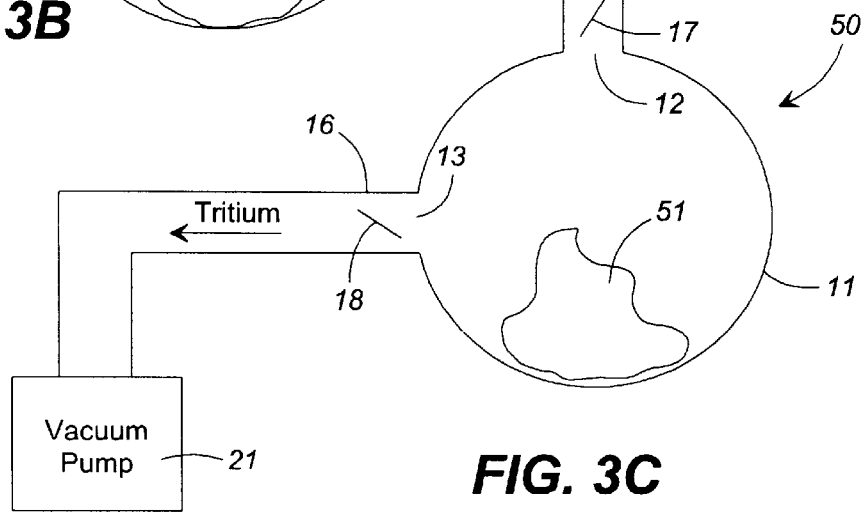
FIG. 3C is a schematic cross-sectional side view of the apparatus of FIG. 1 depicting a third step in radiating an organic mass via the Wilzbach method.

Upon completion of the reaction, the reaction chamber 11 is flushed in a usual way as understood by those skilled in the art, as shown in FIG. 3C. Preferably, the flushing of the chamber 11 begins with evacuating the tritium remaining in the chamber 11. Then, atmospheric gas is introduced back into the chamber 11, removing the vacuum. The polypropylene 51 may then be rinsed, dried and removed from the reaction chamber 11. Upon removal, the radiated polypropylene 51 is then manufactured into the medical device needed. For example, in the case of suture material, the polypropylene 51 may be extruded into a "thread" of the desired length and thickness. Then, the radiated polypropylene suture material is attached to a suture needle and packaged for storage or shipment.

The first and second preferred embodiments involve using the Wilzbach process for generating an entropic exchange of tritium for hydrogen atoms in the medical device structure, or the material to be fashioned into the medical device. As noted above, there are other methods of radiating the medical devices, or the material to be formed into the device. For example, a beta radiating emitting element can be incorporated directly into the backbone of the organic compound. The element of choice in this configuration would be Carbon 12 (C12). Under this procedure, generally, the organic compound is synthesized with C12 as a portion of the material. This compound may then be manufactured into the particular medical device needed. For example, if the compound is polypropylene with C12 in its backbone molecule, then the polypropylene can be extruded into a suture thread. The method of synthesizing an organic compound with a beta emitting element such as C12 is well understood by those with skill in the art and the particular method used in not critical to this aspect of the present invention.

It would be apparent to one skilled in the art that many variations and modifications may be made to the preferred embodiments (i.e. preferred nonlimiting examples) as described above without substantially departing from the principles of the present invention. Such variations and modifications are intended to be included herein and are within the scope of the present invention, as set forth in the following claims.

We claim:

1. A method of creating a medical device that inhibits a hyperplastic response in biological tissue, said method comprising the steps of:
   (a) providing a reaction chamber;
   (b) placing the medical device in said reaction chamber; and
   (c) introducing a beta radiation emitting element into said chamber for causing an entropic exchange process of said beta radiation emitting element for elemental hydrogen in the medical device.

2. The method of claim 1, further comprising the steps of:
   (d) flushing said reaction chamber;
   (e) rinsing the medical device;
   (f) drying the medical device;
   (g) removing the medical device from said reaction chamber; and
   (h) packaging the medical device in a container.

3. The method of claim 1, wherein the medical device comprises a hydrocarbon compound.

4. The method of claim 3, wherein said beta radiation emitting element comprises tritium.

5. The method of claim 4, wherein the medical device comprises a suture device having a suture needle and a suture material.

6. The method of claim 5, wherein said suture material comprises polypropylene.

7. The method of claim 6, wherein said tritium incorporated into said suture material generates beta radiation greater than 0.0002 $\mu$Ci/cm.

8. A method for inhibiting hyperplasia, said method comprising the steps of:
   (a) providing a medical device;
   (b) radiating said medical device such that said medical device emits beta radiation; and
   (c) implanting said medical device into a biological subject, wherein the low radiation emitted from said medical device inhibits localized mitotic cell replication.

9. The method of claim 8, wherein said radiating step comprises:
   (a) providing a reaction chamber;
   (b) placing the medical device in said chamber;
   (c) creating a vacuum in said reaction chamber;
   (d) introducing an ionized beta radiation emitting element into said chamber for causing an entropic exchange process of said beta radiation emitting element for hydrogen in the medical device;
   (e) sealing said reaction chamber;
   (f) removing said ionized beta radiation emitting element from said chamber; and
   (g) removing the medical device from said reaction chamber.

10. The method of claim 9, wherein said medical device comprises a suture device having a suture needle and a suture thread.

11. The method of claim 10, wherein said step of implanting comprises anastomosing an autogenous vein and said inhibiting involves inhibiting an intimal hyperplastic response to the venous graft.

12. The method of claim 8, wherein said ionized beta radiation emitting element comprises tritium.

13. The method of claim 12, wherein said tritium incorporated into the medical device generates beta radiation greater than 0.0002 $\mu$Ci/cm.

14. A medical device for implantation in biological tissue, said medical device comprising:
   (a) an organic compound forming at least a portion of the medical device; and
   (b) a beta radiation emitting element chemically bonded to the medical device, wherein said compound generates a beta radiation greater than 0.0002 $\mu$Ci/cm.

15. The device of claim 14, wherein said beta radiation emitting element comprises carbon 12.

16. The device of claim 14, wherein said organic compound comprises a hydrocarbon compound.

17. The device of claim 16, wherein said beta radiation emitting compound comprises tritium.

18. The device of claim 17, wherein said tritium is incorporated into said hydrocarbon compound by a Wilzbach method.

19. The device of claim 18, wherein the medical device comprises a suture device having a suture needle and a suture material.

20. A method of producing a medical device for inhibiting a hyperplastic response, said method comprising the steps of:
   (a) providing a reaction chamber;
   (b) placing an organic material in said reaction chamber;
   (c) introducing a beta radiation emitting element into said chamber, said element becoming incorporated into said organic material through an entropic exchange process; and
   (d) using said organic material in the manufacture of the medical device.

21. The method of claim 20, wherein said organic material comprises polypropylene.

22. The method of claim 21, wherein said beta radiation emitting element comprises tritium.

* * * * *